US009579147B2

(12) United States Patent
Miller et al.

(10) Patent No.: US 9,579,147 B2
(45) Date of Patent: Feb. 28, 2017

(54) ELECTROSURGICAL FORCEPS WITH TRANSLATING BLADE DRIVER

(71) Applicant: Ethicon Endo-Surgery, Inc., Cincinnati, OH (US)

(72) Inventors: Matthew C. Miller, Cincinnati, OH (US); David A. Witt, Maineville, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 193 days.

(21) Appl. No.: 13/909,576

(22) Filed: Jun. 4, 2013

(65) Prior Publication Data
US 2014/0358142 A1 Dec. 4, 2014

(51) Int. Cl.
*A61B 18/14* (2006.01)
*A61B 17/29* (2006.01)
*A61B 18/00* (2006.01)

(52) U.S. Cl.
CPC ...... *A61B 18/1447* (2013.01); *A61B 18/1442* (2013.01); *A61B 18/1445* (2013.01);
(Continued)

(58) Field of Classification Search
CPC ............ A61B 18/1442; A61B 18/1447; A61B 2018/1442; A61B 2018/145; A61B 2018/1452; A61B 2018/1455; A61B 2018/1457; A61B 2018/146; A61B 2018/1462; A61B 17/28; A61B 17/2812; A61B 17/2816; A61B 17/282; A61B 17/285; A61B 17/29; A61B 17/2909; A61B 17/30; A61B 2017/1125; A61B 2017/22031;
(Continued)

(56) References Cited

U.S. PATENT DOCUMENTS

| 4,805,823 | A | | 2/1989 | Rothfuss |
|---|---|---|---|---|
| 5,318,565 | A | * | 6/1994 | Kuriloff et al. ................. 606/49 |

(Continued)

FOREIGN PATENT DOCUMENTS

| EP | 1897506 | 3/2008 |
|---|---|---|
| WO | WO 2011/044343 | 4/2011 |
| WO | WO 2013/022928 | 2/2013 |

OTHER PUBLICATIONS

U.S. Appl. No. 61/410,603, filed Nov. 5, 2010.
(Continued)

*Primary Examiner* — Jaymi Della
(74) *Attorney, Agent, or Firm* — Frost Brown Todd LLC

(57) ABSTRACT

An apparatus for operating on tissue comprises a body, a lever, an end effector, and a tissue severing assembly. The end effector has a pair of jaws configured to open and close on tissue. The end effector is also capable of delivering RF energy to the tissue. The lever is configured to drive the pair of jaws. The tissue severing assembly comprises a trigger having at least one elongate member, at least one gear, and a firing beam. The trigger may also comprise a button operable to activate the RF energy. The firing beam is operable to sever tissue captured between the jaws. The at least one elongate member, at least one gear, and firing beam are associated such that longitudinal movement of the trigger in a first direction causes longitudinal movement of the firing beam in a second direction.

16 Claims, 13 Drawing Sheets

(52) U.S. Cl.
CPC .................. *A61B 2017/2932* (2013.01); *A61B 2018/00607* (2013.01); *A61B 2018/1455* (2013.01)

(58) Field of Classification Search
CPC ...... A61B 2017/22034; A61B 2017/28; A61B 217/2812; A61B 2017/282; A61B 2017/29; A61B 2017/2926; A61B 2017/30; A61B 10/06
USPC ..................................... 606/50–52, 205–211
See application file for complete search history.

(56) References Cited

U.S. PATENT DOCUMENTS

| | | | |
|---|---|---|---|
| 5,415,334 A | 5/1995 | Williamson, IV et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,358,268 B1* | 3/2002 | Hunt et al. ................ | 606/206 |
| 6,500,176 B1 | 12/2002 | Truckai et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,112,201 B2 | 9/2006 | Truckai et al. | |
| 7,125,409 B2 | 10/2006 | Truckai et al. | |
| 7,143,923 B2 | 12/2006 | Shelton, IV et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,252,667 B2 | 8/2007 | Moses et al. | |
| 7,303,108 B2 | 12/2007 | Shelton, IV et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,613,383 B2 | 12/2013 | Beckman et al. | |
| 2003/0229344 A1* | 12/2003 | Dycus et al. ................ | 606/51 |
| 2005/0119655 A1* | 6/2005 | Moses et al. ................ | 606/51 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0012520 A1* | 1/2009 | Hixson et al. ................ | 606/51 |
| 2010/0106151 A1* | 4/2010 | Longo et al. ................ | 606/33 |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087218 A1 | 4/2011 | Boudreaux et al. | |
| 2011/0276049 A1* | 11/2011 | Gerhardt ................ | 606/45 |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0078248 A1 | 3/2012 | Worrell et al. | |
| 2012/0083783 A1 | 4/2012 | Davison et al. | |
| 2012/0116379 A1 | 5/2012 | Yates et al. | |
| 2012/0330309 A1* | 12/2012 | Joseph ................ | 606/45 |
| 2013/0023868 A1 | 1/2013 | Worrell et al. | |
| 2013/0030428 A1 | 1/2013 | Worrell et al. | |
| 2013/0296922 A1* | 11/2013 | Allen et al. ................ | 606/205 |

OTHER PUBLICATIONS

U.S. Appl. No. 61/550,768, filed Oct. 24, 2011.
International Search Report dated Nov. 27, 2014 for Application No. PCT/US2014/040118, 6 pages.
International Written Opinion dated Nov. 27, 2014 for Application No. PCT/US2014/040118, 10 pages.

* cited by examiner

ELECTROSURGICAL FORCEPS WITH TRANSLATING BLADE DRIVER

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0083783, entitled "Surgical Instrument with Jaw Member," published Apr. 5, 2012, now U.S. Pat. No. 8,888,809, issued Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
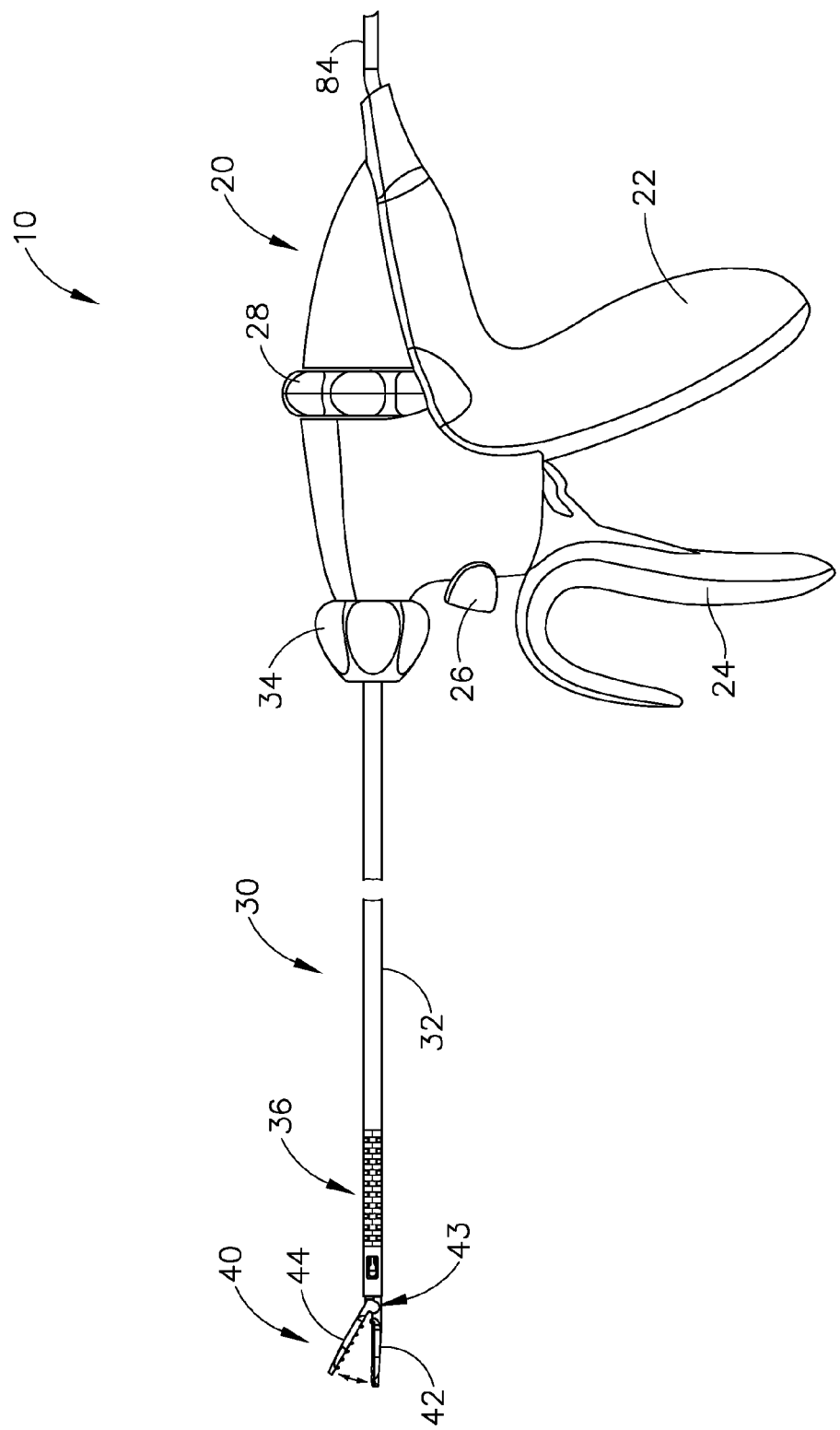
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218; now U.S. Pat. No. 8,939,974, issued Jan. 27, 2015, U.S. Pub. No. 2012/0083783, now U.S. Pat. No. 8,888,809, issued Nov. 18, 2014; U.S. Pub. No. 2012/0116379, now U.S. Pat. No. 9,161,803, issued Oct. 20, 2015; U.S. Pub. No. 2012/0078243; U.S. Pub. No. 2012/0078247, now U.S. Pat. No. 9,402,682, issued Aug. 2, 2016; U.S. Pub. No. 2013/0030428, now U.S. Pat. No. 9,089,327, issued Jul. 28, 2015; and/or U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector

(40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
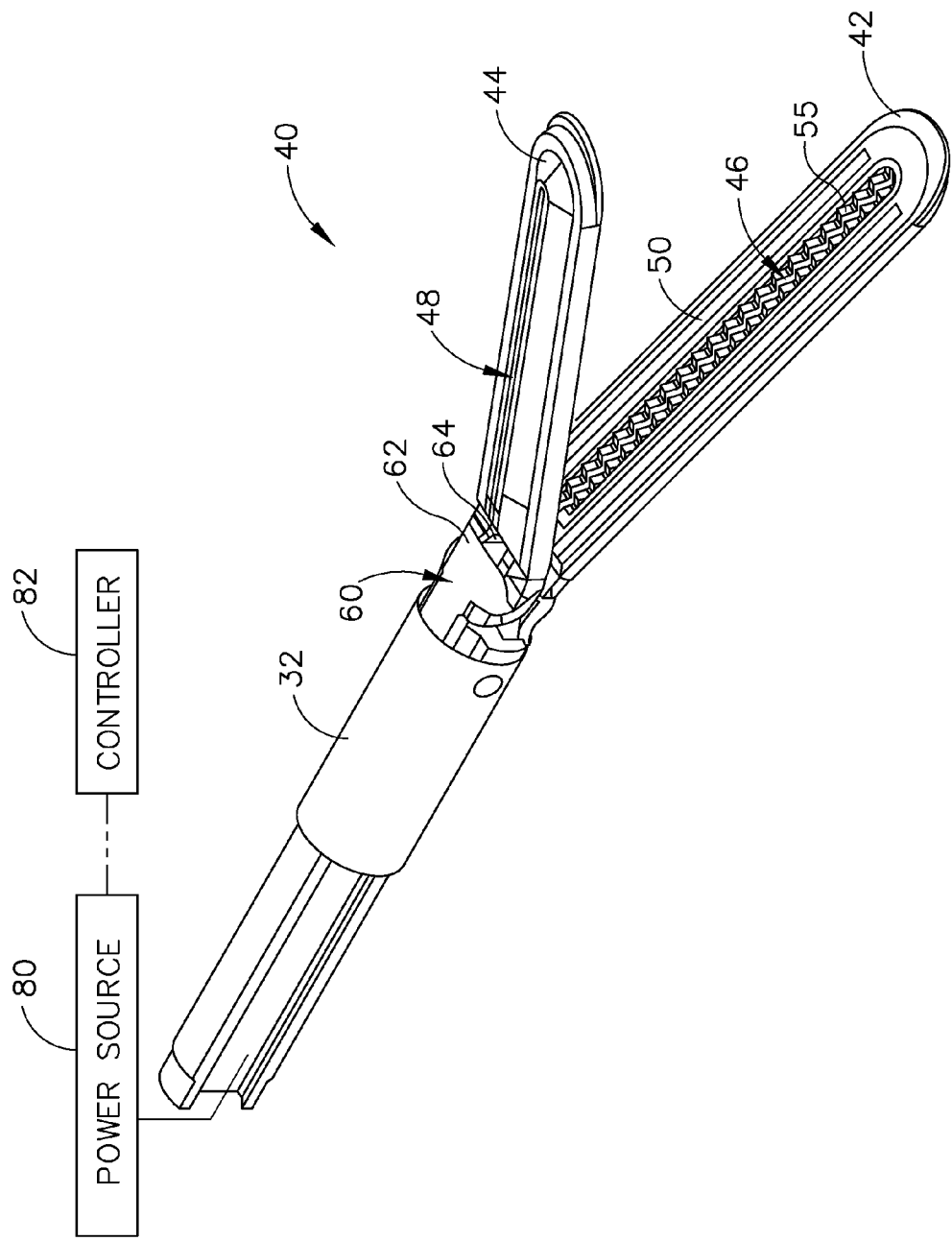
FIG. 2 depicts a perspective view of the end effector of the instrument of FIG. 1, in an open configuration.
Figure 3:
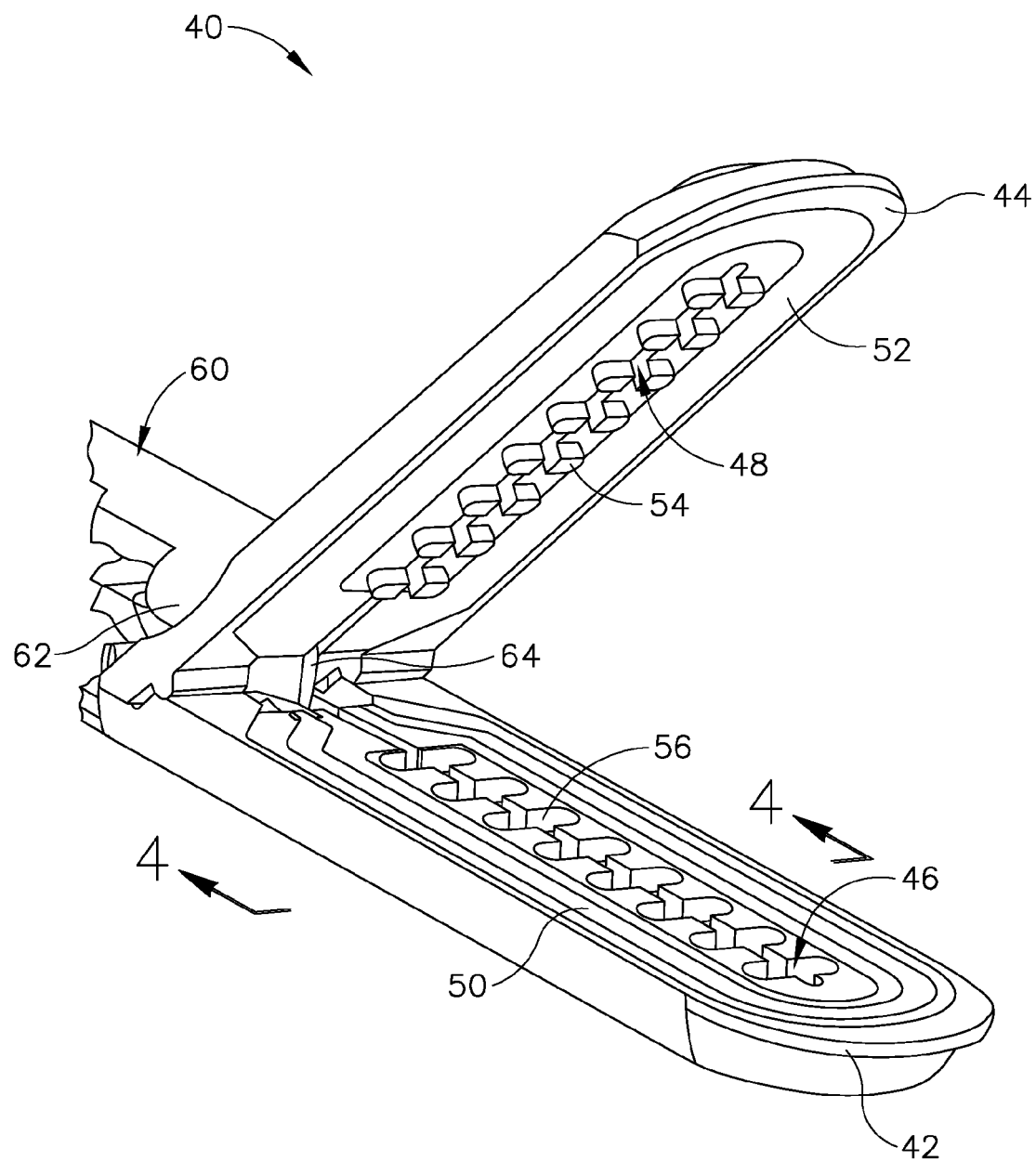
FIG. 3 depicts another perspective view of the end effector of the instrument of FIG. 1, in an open configuration.
Figure 4:
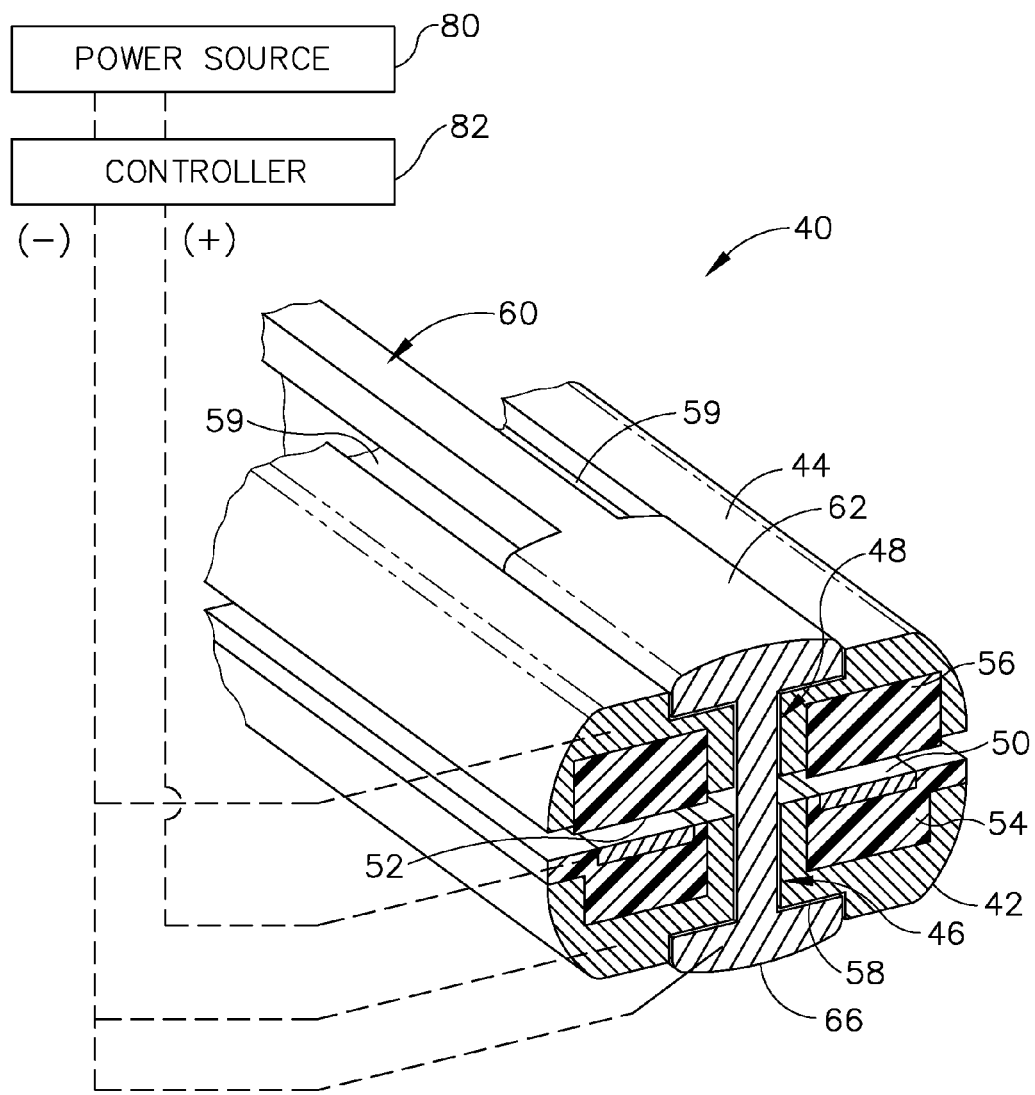
FIG. 4 depicts a cross-sectional end view, taken along line 4-4 of FIG. 3, of the end effector of FIG. 2, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at an active polarity while second electrode surface (52) serves as a reference/return passive electrode, such that RF current flows between electrode surfaces (50, 52) and thereby through tissue captured between jaws (42, 44). There are instances where the active signal crosses zero potential that the reference is at the same potential so there is no current flow. In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44). In some versions, serrations (46, 48) are electrically conductive.

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode.

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
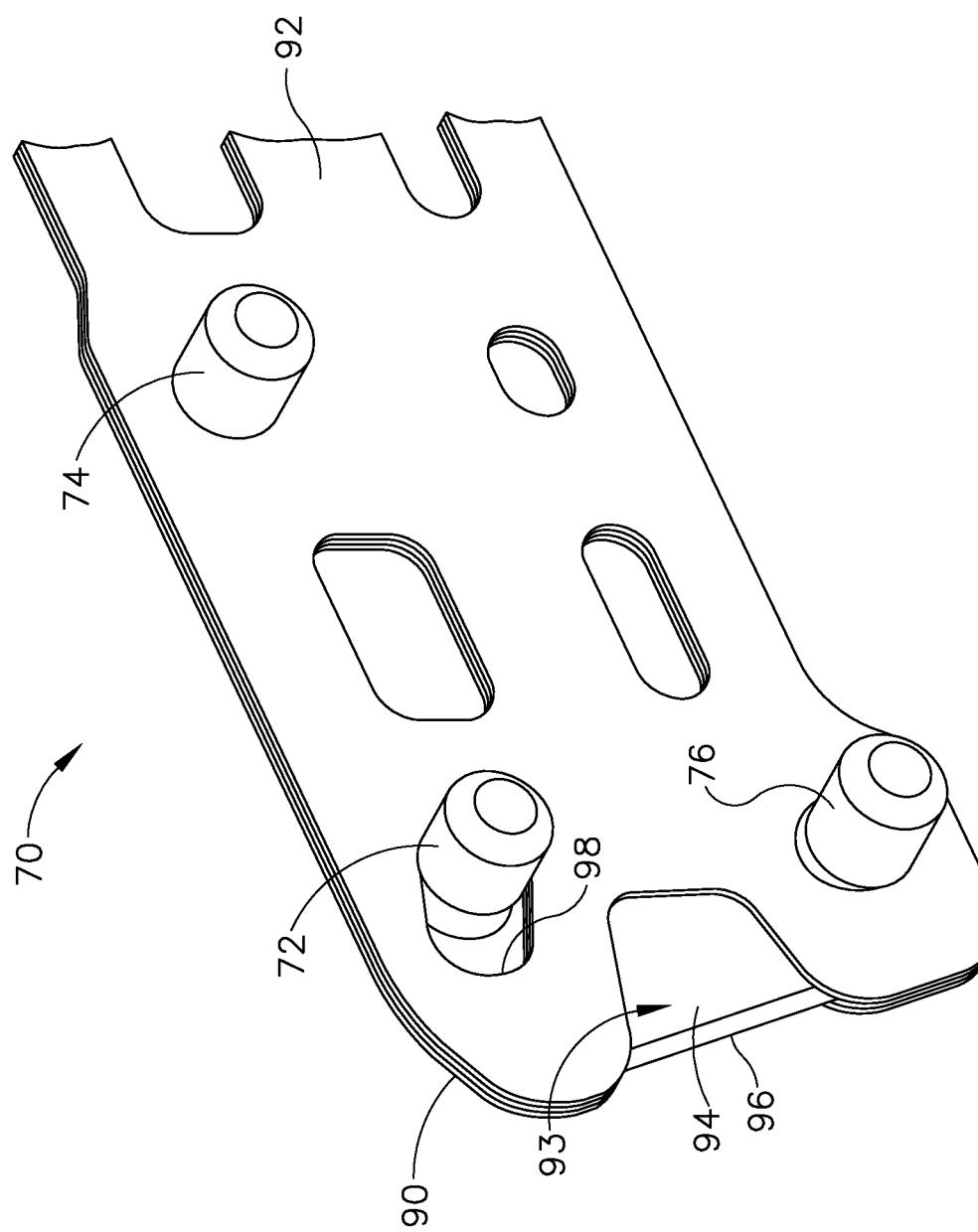
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against recess (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Pins (72, 74, 76) may be pinged, upended, or otherwise configured to provide further retention in the body of firing beam (70). Of course, firing beam (70) may have any other suitable configuration. By way of example only, firing beam (70) may be configured in accordance with at least some of the teachings of U.S. Pub. No. 2012/0083783, now U.S. Pat. No. 8,888,809, issued Nov. 18, 2014, the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, help keep jaws (42, 44) in a closed and tightly clamping position. In particular, flanges (62, 66) help maintain a significantly compressive force between jaws (42, 44). With severed tissue layer portions being compressed between jaws (42, 44), bipolar RF energy is applied to the tissue through electrode surfaces (50, 52) by the user depressing activation button (26). Thus, a bipolar RF current flows through the compressed regions of severed tissue layer portions. The bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Electrosurgical Forceps

As a variation of instrument (10) discussed above, instrument (10) may be arranged as an electrosurgical forceps. For instance, handpiece (20) may be reconfigured from a pistol grip configuration to a scissor grip configuration. In addition, shaft (30) may be reconfigured as a pair of pivoting scissor arms. Various examples of how instrument (10) may be reconfigured as an electrosurgical forceps will be described in greater detail below; while other examples will be apparent to those of ordinary skill in the art according to the teachings herein. It should be understood that the electrosurgical forceps examples described below may function substantially similar to instrument (10) described above. In particular, the electrosurgical forceps described below may be used to grasp and clamp tissue, seal the tissue with bipolar RF energy, and cut the tissue with a translating firing beam.

Figure 6A:
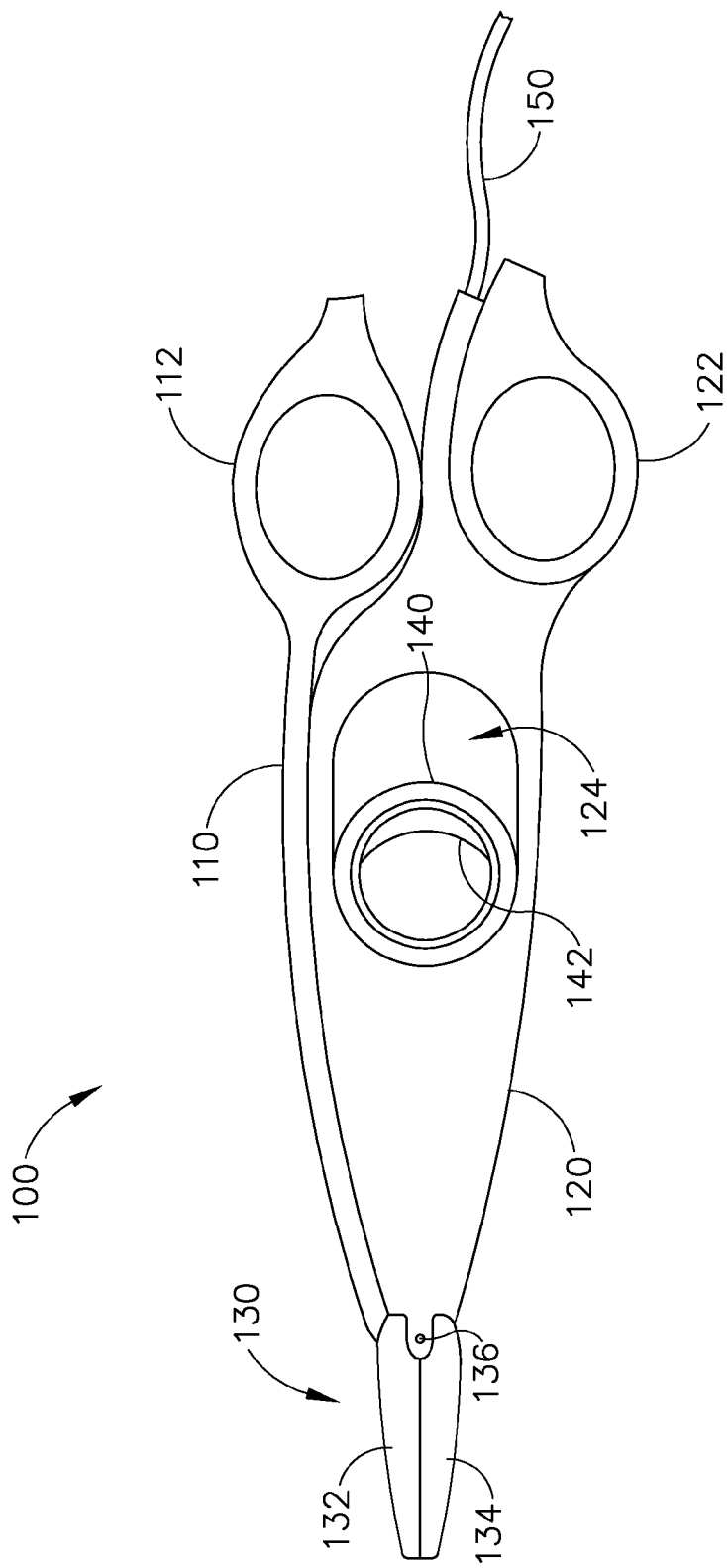
FIG. 6A depicts a side elevational view of an exemplary electrosurgical forceps variation of the instrument of FIG. 1 in a closed position.

One merely exemplary variation of an electrosurgical forceps (100) is shown in FIGS. 6A-7B. Forceps (100) of the present example comprise a body (120), a lever (110), an end effector (130), and a trigger (140). End effector (130) is disposed at a distal end of body (120). Body (120) of the present example includes a grip (122) at a proximal end of body (120). Lever (110) of the present example includes a grip (112) at a proximal end of lever (110). Lever (110) is pivotable toward and away from body (120) to selectively open and close end effector (130) as will be described in greater detail below. An activation button (142) is operable to selectively activate RF circuitry that is in communication with end effector (130), as will also be described in greater detail below. In some versions, button (142) also serves as a mechanical lockout against trigger (140), such that trigger (140) cannot be actuated unless button (142) is being pressed simultaneously. As shown in FIG. 6A-6B, trigger (140) is slidably disposed with an elongate slot (124) of body (120). It should be understood that trigger (140) may slide longitudinally relative to body (120) within elongate slot (124). Longitudinal channels (not shown), although not necessary, may be defined within the internal surface of elongate slot (124) such that trigger (140) may be guided within the longitudinal channels. Forceps (100) may be coupled with an electrical source (not shown) and a controller (not shown) via a cable (150), which extends proximally from body (120).

A. Exemplary End Effector

Figure 6B:
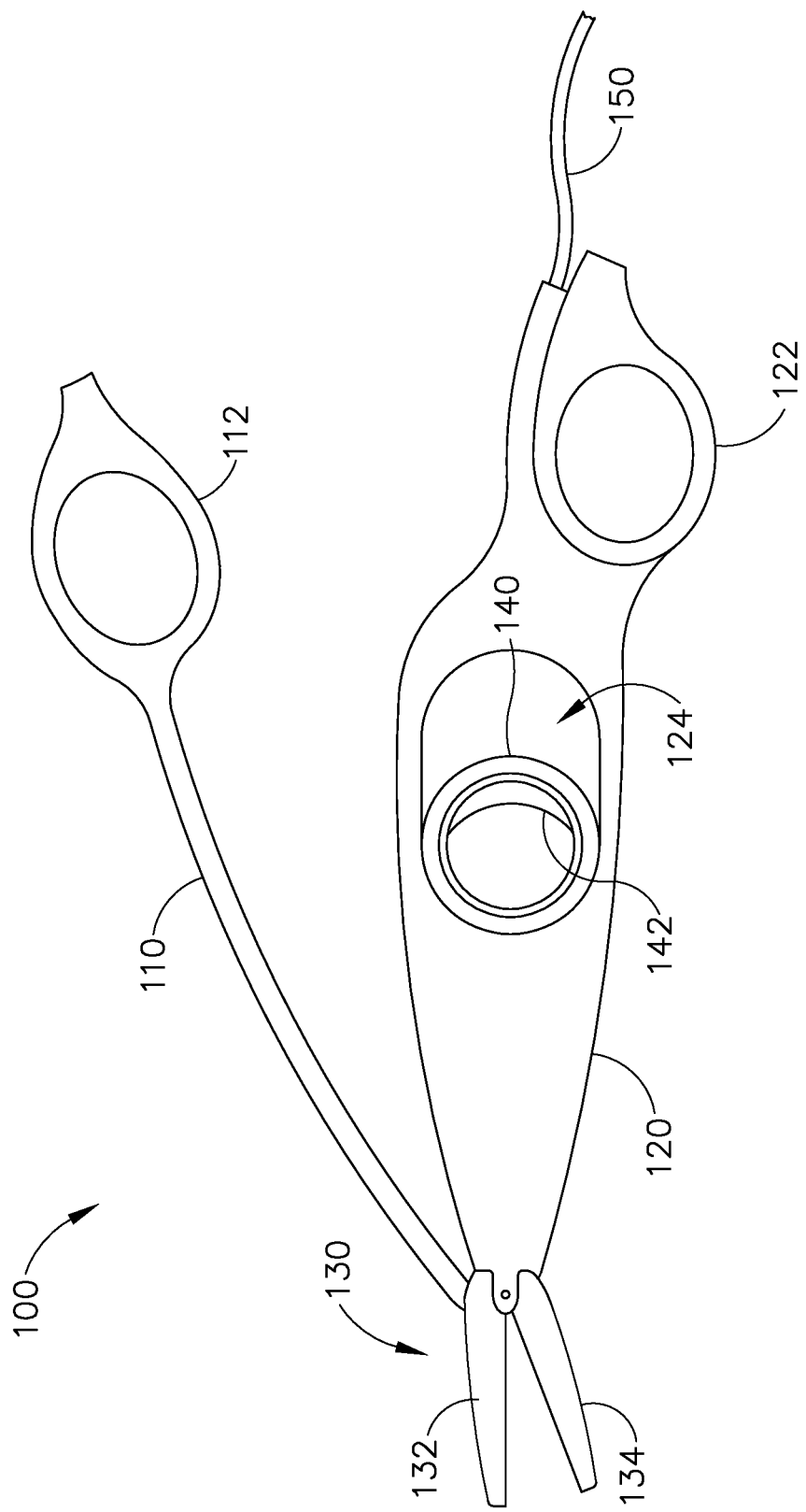
FIG. 6B depicts a side elevational view of the electrosurgical forceps of FIG. 6A in an open position.

End effector (130) of the present example comprises a first jaw (134) and a second jaw (132). First jaw (134) is configured to operate substantially similar to first jaw (42) as discussed above with reference to instrument (10) and second jaw (132) is configured to operate substantially similar to second jaw (44) as discussed above with reference to instrument (10), except for the differences discussed below. In the present example, second jaw (132) is substantially fixed relative to body (120); while first jaw (134) pivots relative to body (120), toward and away from second jaw (132). Lever (110) is configured to pivot about an axis that is defined by a pin (or similar feature) (136). First jaw (134) also pivots about the axis that is defined by pin (136). As shown in FIG. 6B, first jaw (134) is coupled to lever (110) at a distal end of lever (110) such that as lever (110) pivots about the axis that is defined by pin (136), first jaw (134) pivots as well. During an exemplary operation, lever (110) may drive first jaw (134) from a closed position as shown in FIG. 6A, to an open position as shown in FIG. 6B, and back to the closed position as shown in FIG. 6A. In some versions, lever (110) also serves as a mechanical lockout against trigger (140) and/or button (142), such that trigger (140) and/or button (142) cannot be actuated unless lever (110) is in the closed position as shown in FIG. 6A.

B. Exemplary Firing Beam

1. Exemplary Activation Apparatus

Figure 7A:
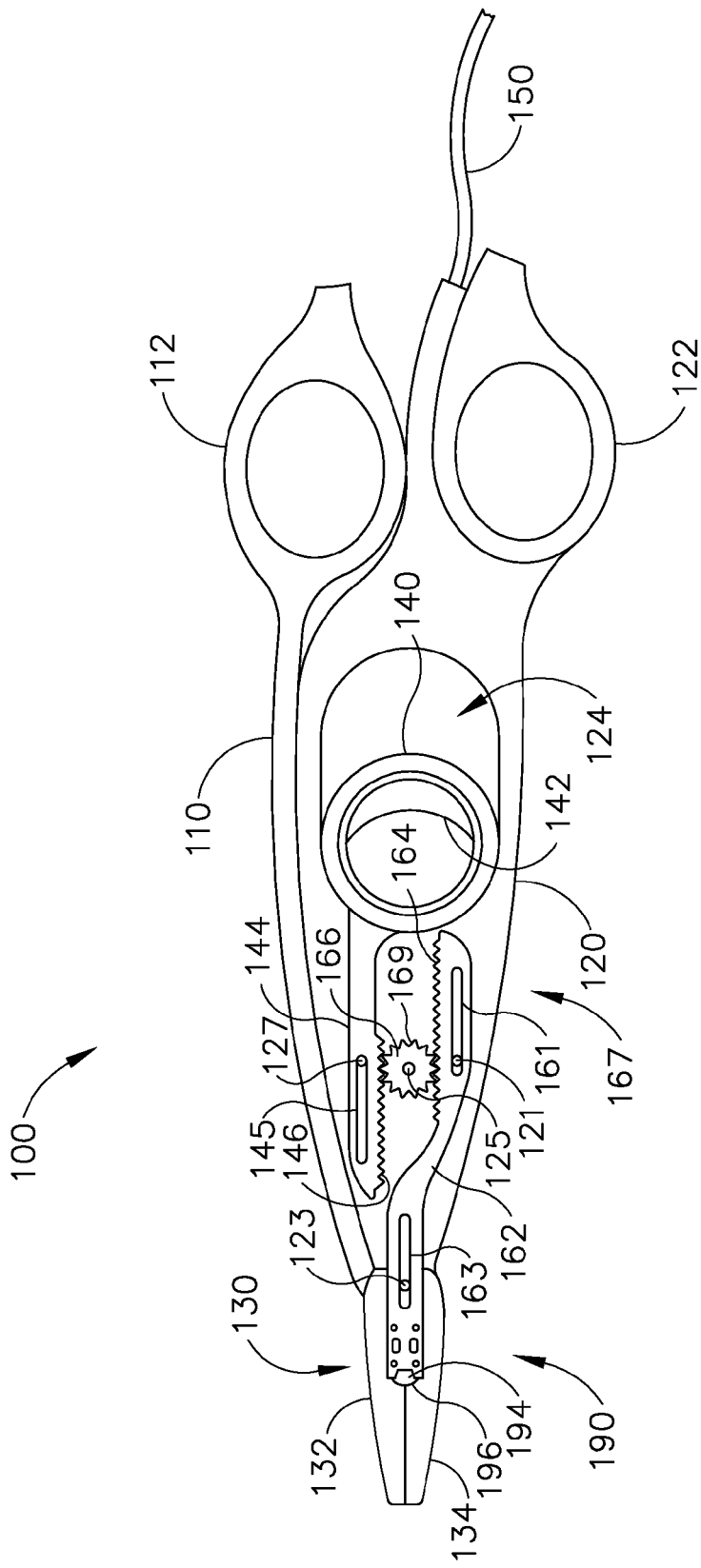
FIG. 7A depicts a side cross-sectional view of the electrosurgical forceps of FIG. 6A, showing an exemplary knife activation apparatus in a first position.
Figure 7B:
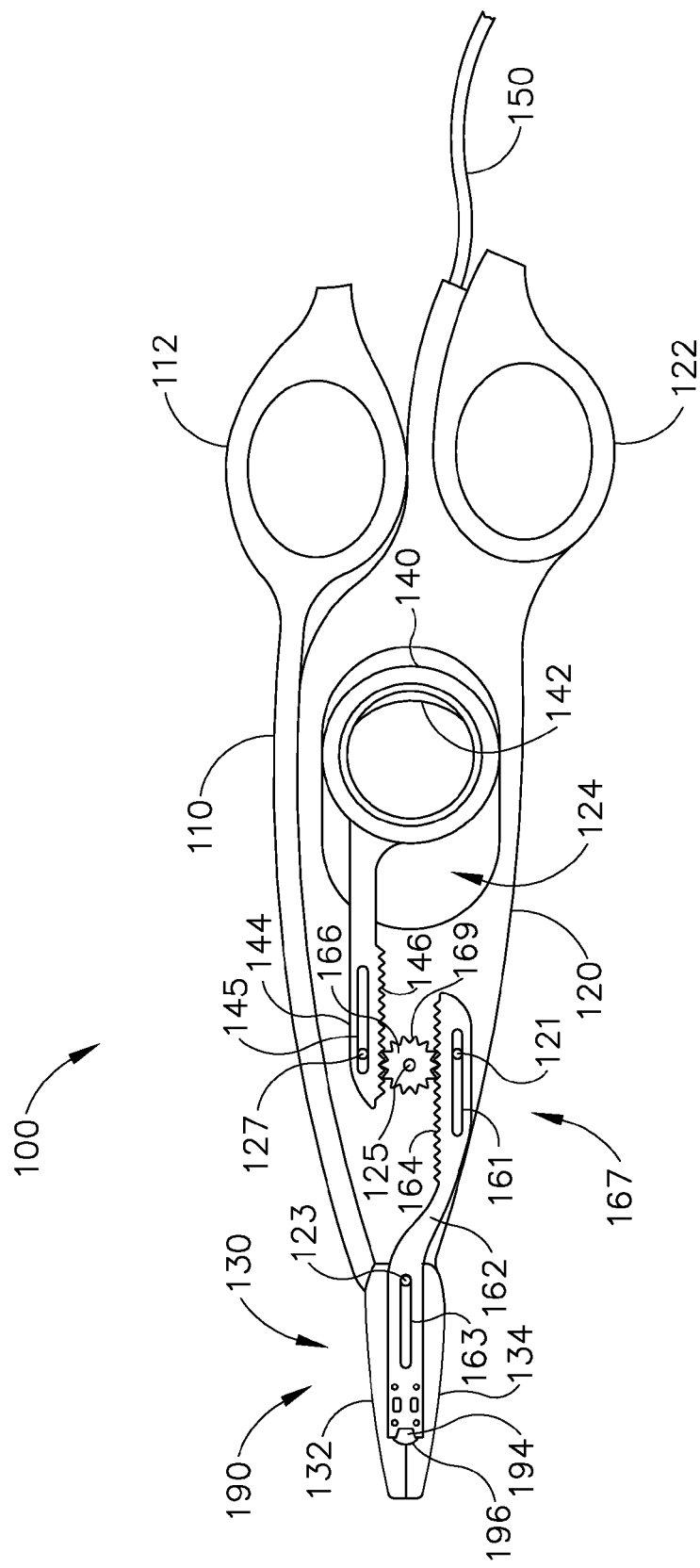
FIG. 7B depicts a side cross-sectional view of the electrosurgical forceps of FIG. 6A, showing the exemplary knife activation apparatus of FIG. 7A in a second position.

As seen in FIGS. 7A-7B, forceps (100) of the present example include a firing beam (162) that is longitudinally movable along part of the length of end effector (130). Firing beam (162) is configured to operate substantially similar to firing beam (70) as discussed above with reference to instrument (10). Firing beam (162) is positioned within body (120) and translates longitudinally within body (120). Firing beam (162) comprises a proximal portion (167) and a distal portion (190). Distal portion (190) of firing beam (162) comprises a blade insert (194) having a sharp distal edge (196) such that blade insert (194) will readily sever tissue that is captured between first jaw (134) and second jaw (132) as firing beam (162) is advanced distally. Firing beam (162) presents a first slot (161) within proximal portion (167) and a second slot (163) within distal portion (190). Body (120) presents a first pin (121) and a second pin (123). Pins (121, 123) are slidably disposed within respective slots (161, 163) such that firing beam (162) may slide longitudinally within body (120). Although the present example utilizes slots (161, 163) and pins (121, 123) to guide firing beam (162), it should be understood that other methods of guiding firing beam (162) may be utilized and would be apparent to those of ordinary skill in the art in view of the teachings herein. For instance, body (120) may present a series of channels (not shown) within which firing beam (162) could slide.

As shown in FIG. 7A, proximal portion (167) of firing beam (162) also comprises a plurality of teeth (164) that form a rack. A gear (166) is disposed within body (120) and rotates about a third pin (125). Gear (166) comprises a plurality of teeth (169). Teeth (169) of gear (166) engage teeth (164) of firing beam (162) in a rack and pinion relationship. An elongate member (144) extends distally from trigger (140). Elongate member (144) presents a third slot (145). Body (120) presents a fourth pin (127). Fourth pin (127) is slidably disposed within third slot (145) such that elongate member (144) may slide longitudinally within body (120). Although the present example utilizes slot (145) and pin (127) to guide elongate member (144), it should be understood that other methods of guiding elongate member (144) may be utilized and would be apparent to those of ordinary skill in the art in view of the teachings herein. For instance, body (120) may present a channel within which elongate member (144) could slide. Elongate member (144) comprises a plurality of teeth (146). Teeth (169) of gear (166) engage teeth (146) of elongate member (144) in a rack and pinion relationship. As shown in FIG. 7A, teeth (164) of firing beam (162) and teeth (146) of elongate member (144) engage teeth (169) of gear (166) on opposites sides of gear (166). Therefore, it should be understood that longitudinal movement of elongate member (144) in a first direction will cause longitudinal movement of firing beam (162) in a second direction.

As discussed above, trigger (140) may slide longitudinally relative to body (120) within elongate slot (124). Initially, trigger (140) remains in a distal position as shown in FIG. 7A. When trigger (140) is in this distal position, firing beam (162) remains in a proximal position as shown in FIG. 7A. Once tissue has been captured between first jaw (134) and second jaw (132), the user may begin to pull trigger (140) in a proximal direction within elongate slot (124). As the user begins to pull trigger (140) proximally, the force required to do so will cause button (142) to be depressed thereby causing RF energy to be delivered into the tissue captured between first jaw (134) and second jaw (132) via electrodes in jaws (132, 134). Therefore it should be understood that RF energy will be delivered into the tissue captured between first jaw (134) and second jaw (132) prior to the tissue being severed by blade insert (194). As the user continues to pull trigger (140) proximally, button (142) remains depressed and RF energy is continually delivered to the tissue captured between first jaw (134) and second jaw (132).

As trigger (140) is moved into a proximal position as shown in FIG. 7B, the longitudinal movement of trigger (140) causes elongate member (144) to be moved proximally as well. This proximal longitudinal movement of elongate member (144) causes gear (166) to be rotated in a clock-wise (CW) direction about third pin (125). This CW rotation of gear (166) causes distal longitudinal movement of firing beam (162). Such distal longitudinal movement of firing beam (162) will drive blade insert (194) to sever the tissue captured between first jaw (134) and second jaw (132). After the tissue has been severed, the user may draw firing beam (162) proximally by moving trigger (140) distally. While FIG. 7B shows a particular distance between sharp distal edge (196) and the distal tips of jaws (132, 134) upon completion of the distal advancement stroke of firing beam (162), it should be understood that forceps (100) may be configured such that this distance may be reduced relative to what is shown in FIG. 7B. For instance, forceps (100) may be configured such that sharp distal edge (196) reaches the distal tips of jaws (132, 134) (or a location just barely proximal to the distal tips of jaws (132, 134)) upon completion of the distal advancement stroke of firing beam (162). This may reduce any likelihood of tissue between jaws (132, 134) being left unsevered upon completion of the distal advancement stroke of firing beam (162).

The steps of capturing tissue between first jaw (134) and second jaw (132), severing tissue with blade insert (194), and drawing firing beam (162) from the tissue, may be repeated as many times as desired. It should be understood that, although in the present example the user manually draws firing beam (162) proximally from the tissue by moving trigger (140) distally, such proximal movement of firing beam (162) may be caused by a biasing member (not shown) which drives trigger (140) in a distal direction once the user has released trigger (140). For instance, a spring, or a plurality of springs, may be positioned to bias trigger (140) distally.

2. First Exemplary Alternative Activation Apparatus

Figure 8A:
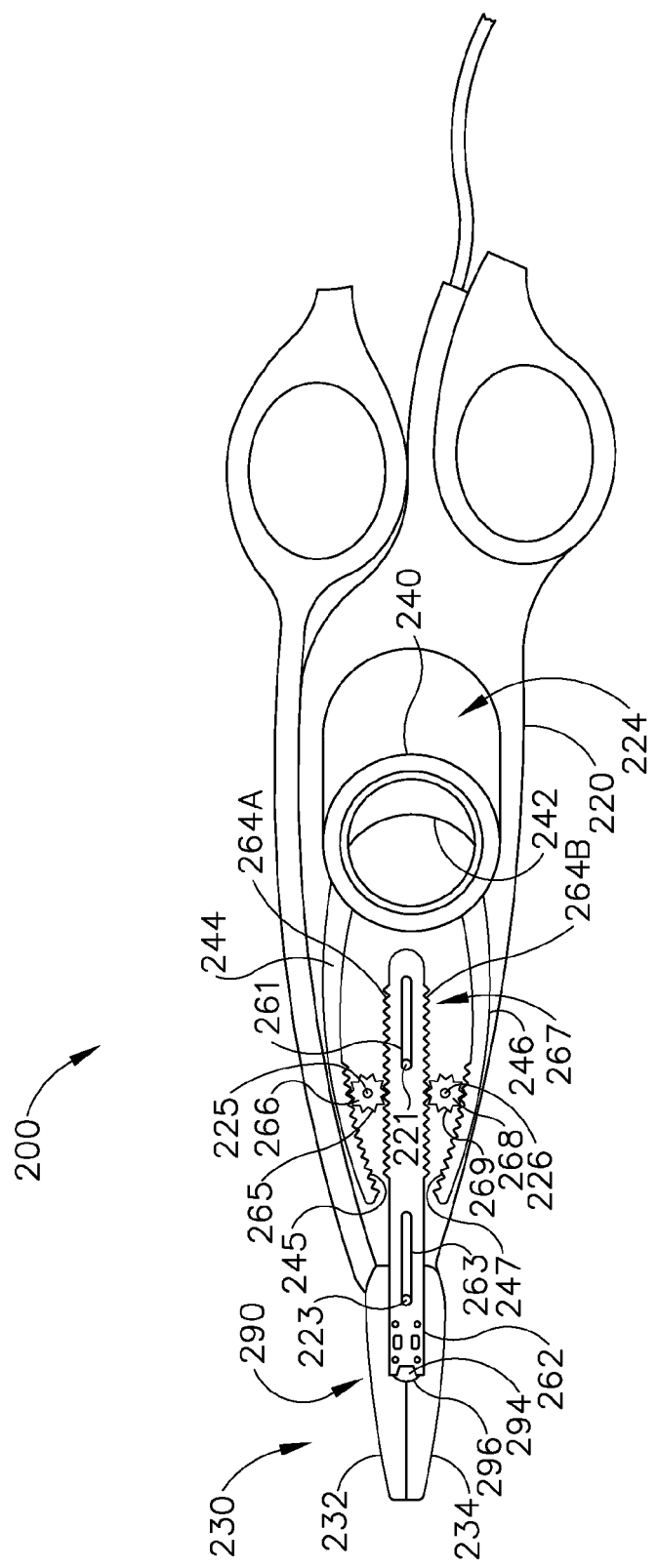
FIG. 8A depicts a side cross-sectional view of another exemplary electrosurgical forceps variation of the instrument of FIG. 1, showing an exemplary alternative knife activation apparatus in a first position.
Figure 8B:
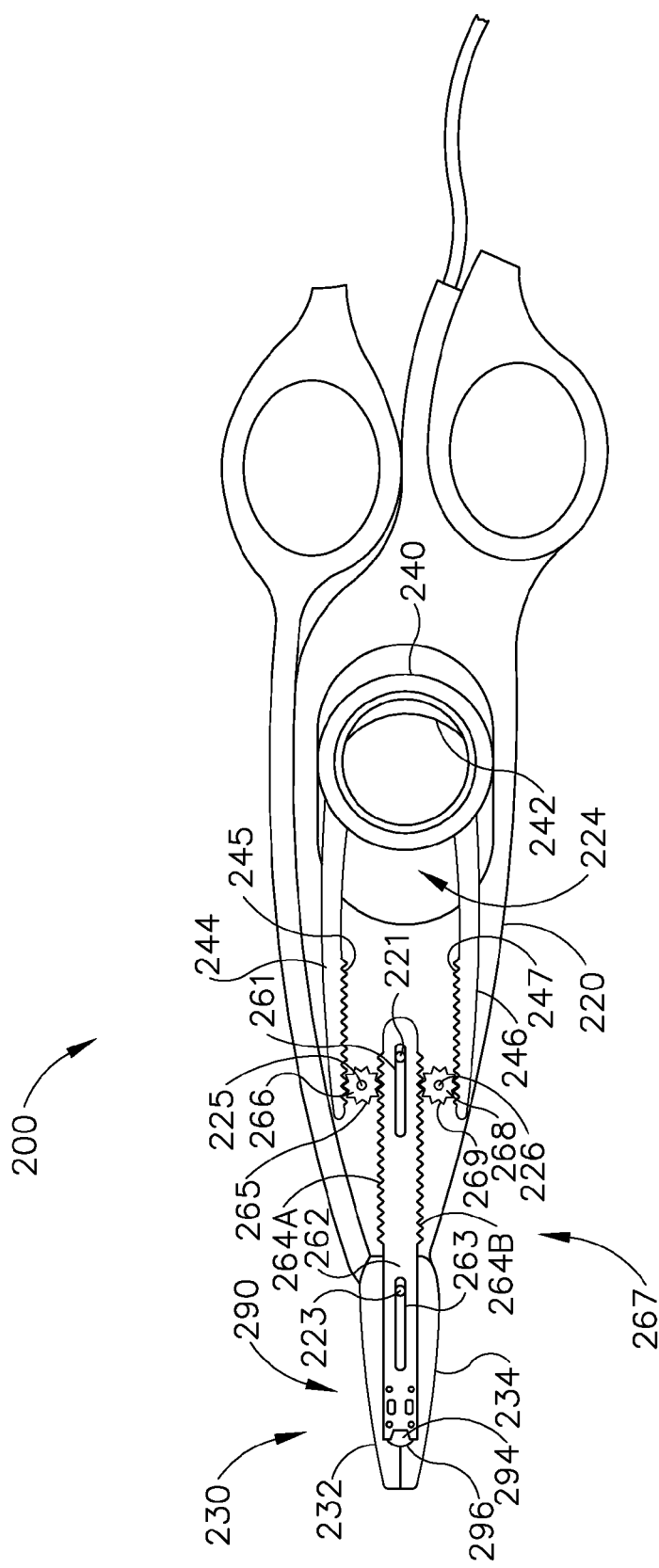
FIG. 8B depicts a side cross-sectional view of the electrosurgical forceps of FIG. 8A, showing the knife activation apparatus of FIG. 8A in a second position.

An exemplary alternative pair of electrosurgical forceps (200) is shown in FIG. 8A-8B. Forceps (200) and the components discussed below are configured to operate substantially similar to forceps (100) discussed above except for the differences discussed below. As seen in FIGS. 8A-8B, forceps (200) include a firing beam (262) that is longitudinally movable along part of the length of an end effector (230). Firing beam (262) is configured to operate substantially similar to firing beam (70) as discussed above with reference to instrument (10). Firing beam (262) is positioned within a body (220) and translates longitudinally within body (220). Firing beam (262) comprises a proximal portion (267) and a distal portion (290). Distal portion (290) of firing beam (262) comprises a blade insert (294) having a sharp distal edge (296) such that blade insert (294) will readily sever tissue that is captured between a first jaw (234) and a second jaw (232) as firing beam (262) is advanced distally. Firing beam (262) presents a first slot (261) within proximal portion (267) and a second slot (263) within distal portion (290). Body (220) presents a first pin (221) and a second pin (223). Pins (221, 223) are slidably disposed within respective slots (261, 263) such that firing beam (262) may slide longitudinally within body (220). Although the present example utilizes slots (261, 263) and pins (221, 223) to guide firing beam (262), it should be understood that other methods of guiding firing beam (262) may be utilized and would be apparent to those of ordinary skill in the art in view of the teachings herein. For instance, body (220) may present a channel (not shown) within which firing beam (262) could slide.

As shown in FIG. 8A, proximal portion (267) of firing beam (262) comprises a first plurality of teeth (264A) on a first side of firing beam (262) and a second plurality of teeth (264B) on a second side of firing beam (262). A first gear (266) is disposed within body (220) and rotates about a third pin (225). First gear (266) comprises a plurality of teeth (265). A second gear (268) is disposed within body (220) and rotates about a fourth pin (226). Second gear (268) comprises a plurality of teeth (269). Teeth (265) of first gear (266) engage first plurality of teeth (264A) of firing beam (262) in a rack and pinion relationship. Teeth (269) of second gear (268) engage teeth (264B) of firing beam (262) in a rack and pinion relationship.

A first elongate member (244) extends distally from a trigger (240). First elongate member (244) comprises a plurality of teeth (245). Teeth (265) of first gear (266) engage teeth (245) of first elongate member (244) in a rack and pinion relationship. A second elongate member (246) also extends distally from trigger (240). Second elongate member (246) comprises a plurality of teeth (247). Teeth (269) of second gear (268) engage teeth (247) of second elongate member (246) in a rack and pinion relationship. Both first elongate member (244) and second elongate member (246) are inwardly biased toward firing beam (262) such that first elongate member (244) and second elongate member (246) remain in contact with first gear (266) and second gear (268) respectively. This inward bias of first elongate member (244) and second elongate member (246) allows for a distal portion of forceps (200) to have a reduced cross-sectional area. As shown in FIG. 8A, first plurality of teeth (264A) of firing beam (262) and teeth (245) of first elongate member (244) engage teeth (265) of first gear (266) on opposites sides of first gear (266). Also as shown in FIG. 8A, second plurality of teeth (264B) of firing beam (262) and teeth (247) of second elongate member (246) engage teeth (269) of second gear (268) on opposites sides of second gear (268). Therefore, it should be understood that longitudinal movement of first elongate member (244) and second elongate member (246) in a first direction will cause longitudinal movement of firing beam (262) in a second direction.

Trigger (240) may slide longitudinally relative to body (220) within an elongate slot (224). Initially, trigger (240) remains in a distal position as shown in FIG. 8A. When trigger (240) is in this distal position, firing beam (262) remains in a proximal position as shown in FIG. 8A. Once tissue has been captured between first jaw (234) and second jaw (232), the user may begin to pull trigger (240) in a proximal direction within elongate slot (224). As the user begins to pull trigger (240) proximally, the force required to do so will cause a button (242) to be depressed thereby causing RF energy to be delivered into the tissue captured between first jaw (234) and second jaw (232) via electrodes in jaws (232, 234). Therefore, it should be understood that RF energy will be delivered into the tissue captured between first jaw (234) and second jaw (232) prior to the tissue being severed by blade insert (294). As the user continues to pull trigger (240) proximally, button (242) remains depressed and RF energy is continually delivered to the tissue captured between first jaw (234) and second jaw (232).

As trigger (240) is moved into a proximal position as shown in FIG. 8B, the longitudinal movement of trigger (240) causes first elongate member (244) and second elongate member (264) to be moved proximally as well. The resilience of first elongate member (244) and second elongate member (246) causes first elongate member (244) and second elongate member (246) to remain in contact with first gear (266) and second gear (268), respectively; while the flexibility of first elongate member (244) and second elongate member (246) allow first elongate member (244) and second elongate member (246) to flex outwardly during the transition of trigger (240) from the position shown in FIG. 8A to the position shown in FIG. 8B. The proximal longitudinal movement of first elongate member (244) causes first gear (266) to be rotated in a CW direction about third pin (225). The proximal longitudinal movement of second elongate member (246) causes second gear (268) to be rotated in a Counter-Clockwise (CCW) direction about fourth pin (226). The combination of CW rotation of first gear (266) and CCW rotation of second gear (268) causes distal longitudinal movement of firing beam (262). Such distal longitudinal movement of firing beam (262) will drive blade insert (294) to sever the tissue captured between first jaw (234) and second jaw (232). After the tissue has been severed, the user may draw firing beam (262) proximally by moving trigger (240) distally. The resilience of first elongate member (244) and second elongate member (246) causes first elongate member (244) and second elongate member (246) to return to the inwardly biased position as shown in FIG. 8A.

While FIG. 8B shows a particular distance between sharp distal edge (296) and the distal tips of jaws (232, 234) upon completion of the distal advancement stroke of firing beam (262), it should be understood that forceps (200) may be configured such that this distance may be reduced relative to what is shown in FIG. 8B. For instance, forceps (200) may be configured such that sharp distal edge (296) reaches the distal tips of jaws (232, 234) (or a location just barely proximal to the distal tips of jaws (232, 234)) upon completion of the distal advancement stroke of firing beam (262). This may reduce any likelihood of tissue between jaws (232, 234) being left unsevered upon completion of the distal advancement stroke of firing beam (262).

The steps of capturing tissue between first jaw (234) and second jaw (232), severing tissue with blade insert (294), and drawing firing beam (262) from the tissue, may be repeated as many times as desired. It should be understood, that although in the present example the user manually draws firing beam (262) proximally from the tissue by moving trigger (240) distally, such proximal movement of firing beam (262) may be caused by a biasing member (not shown) which drives trigger (240) in a distal direction once the user has released trigger (240). For instance, a spring, or a plurality of springs, may be positioned to bias trigger (240) distally.

3. Second Exemplary Alternative Activation Apparatus

Figure 9A:
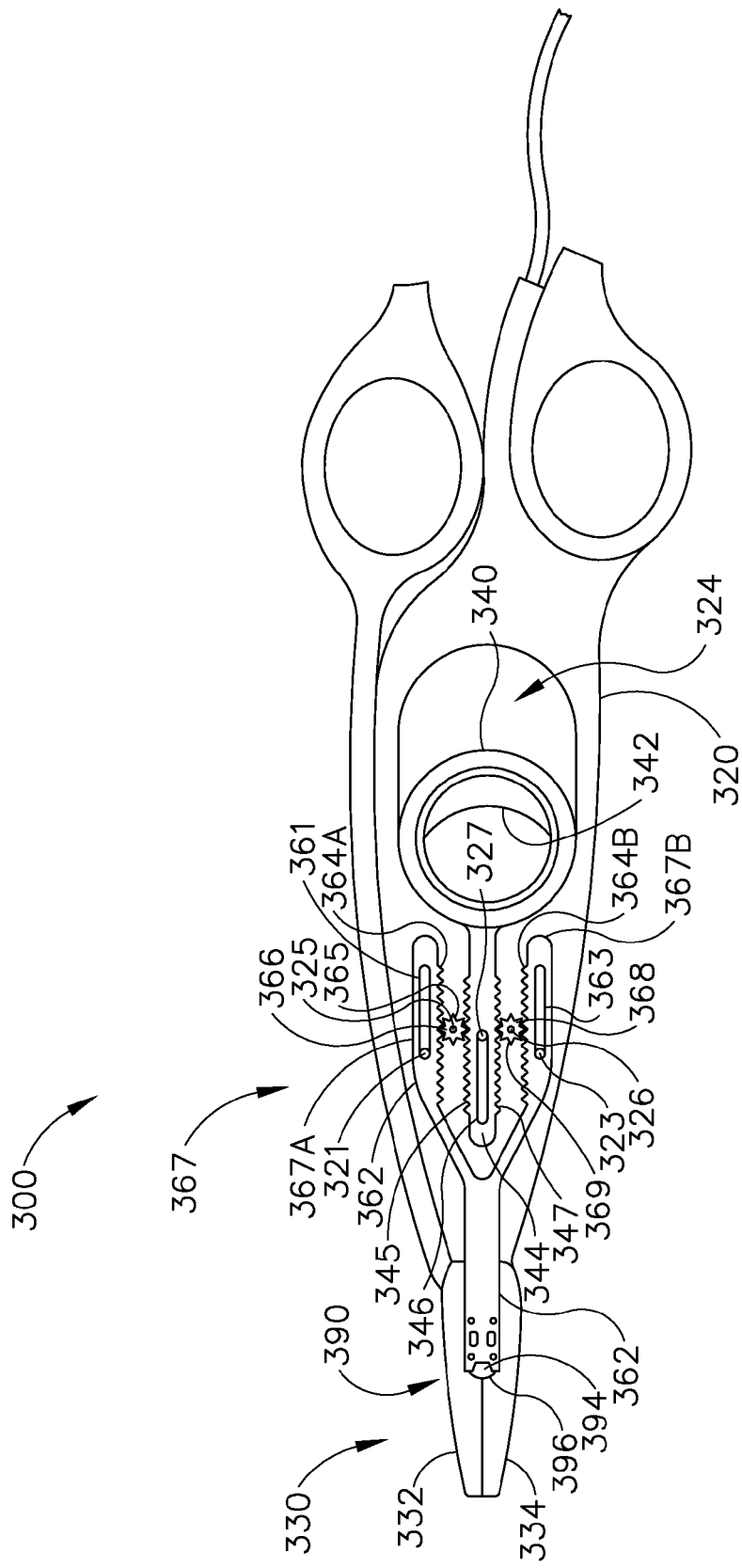
FIG. 9A depicts a side cross-sectional view of yet another exemplary electrosurgical forceps variation of the instrument of FIG. 1, showing another exemplary alternative knife activation apparatus in a first position.
Figure 9B:
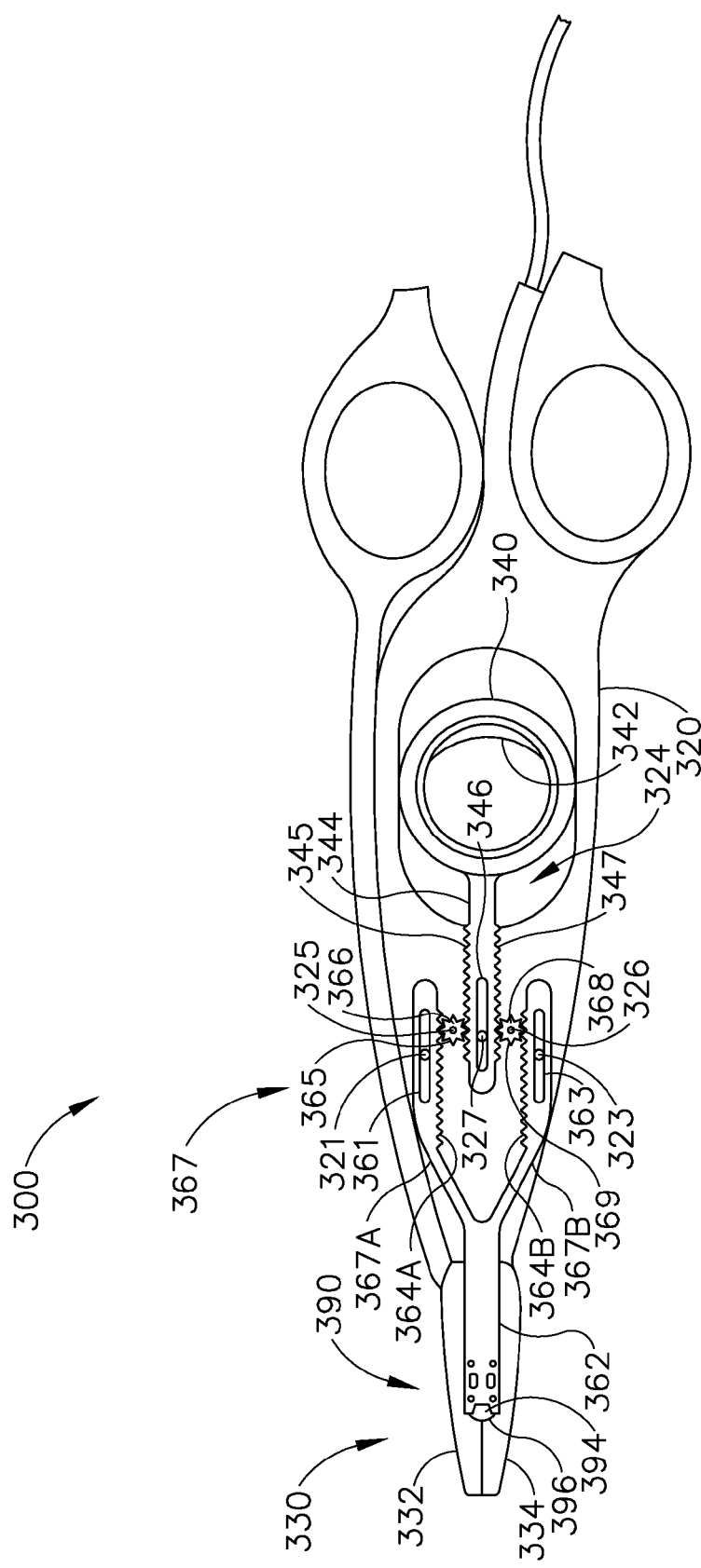
FIG. 9B depicts a side cross-sectional view of the electrosurgical forceps of FIG. 9A, showing the knife activation apparatus of FIG. 9A in a second position.

Another exemplary alternative pair of electrosurgical forceps (300) is shown in FIG. 9A-9B. Forceps (300) and the components discussed below are configured to operate substantially similar to forceps (100) discussed above except for the differences discussed below. As seen in FIGS. 9A-9B, forceps (300) include a firing beam (362) that is longitudinally movable along part of the length of an end effector (330). Firing beam (362) is configured to operate substantially similar to firing beam (70) as discussed above with reference to instrument (10). Firing beam (362) is positioned within a body (320) and translates longitudinally within body (320). Firing beam (362) comprises a proximal portion (367) and a distal portion (390). Proximal portion (367) of firing beam (362) includes a first arm (367A) and a second arm (367B). Distal portion (390) of firing beam (362) comprises a blade insert (394) having a sharp distal edge (396) such that blade insert (394) will readily sever tissue that is captured between a first jaw (334) and a second jaw (332) as firing beam (362) is advanced distally. Firing beam (362) presents a first slot (361) within first arm (367A) of proximal portion (367) and a second slot (363) within second arm (367B) of proximal portion (367). Body (320) presents a first pin (321) and a second pin (323). Pins (321, 323) are slidably disposed within respective slots (361, 363) such that firing beam (362) may slide longitudinally within body (320). Although the present example utilizes slots (361, 363) and pins (321, 323) to guide firing beam (362), it should be understood that other methods of guiding firing beam (362) may be utilized and would be apparent to those of ordinary skill in the art in view of the teachings herein. For instance, body (320) may present a channel (not shown) within which firing beam (362) could slide.

As shown in FIG. 9A, first arm (367A) of proximal portion (367) of firing beam (362) comprises a first plurality of teeth (364A). A first gear (366) is disposed within body (320) and rotates about a third pin (325). First gear (366) comprises a plurality of teeth (365). Teeth (365) of first gear (366) engage first plurality of teeth (364A) of firing beam (362) in a rack and pinion relationship. Second arm (367B) of proximal portion (367) of firing beam (362) comprises a second plurality of teeth (364B). A second gear (368) is disposed within body (320) and rotates about a fourth pin (326). Second gear (368) comprises a plurality of teeth (369). Teeth (369) of second gear (368) engage teeth (364B) of firing beam (362) of firing beam (362) in a rack and pinion relationship.

An elongate member (344) extends distally from a trigger (340). Elongate member (344) presents a third slot (346). Body (320) presents a fifth pin (327). Fifth pin (327) is slidably disposed within third slot (346) such that elongate member (344) may slide longitudinally within body (320). Although the present example utilizes slot (346) and fifth pin (327) to guide elongate member (344), it should be understood that other methods of guiding elongate member (344) may be utilized and would be apparent to those of ordinary skill in the art in view of the teachings herein. For instance, body (320) may present a channel within which elongate member (344) could slide.

Elongate member (344) comprises a first plurality of teeth (345) on a first side of elongate member (344) and a second plurality of teeth (347) on a second side of elongate member (344). Teeth (365) of first gear (366) engage first plurality of teeth (345) of elongate member (344) in a rack and pinion relationship. Teeth (369) of second gear (368) engage second plurality of teeth (347) of elongate member (344) in a rack an pinion relationship. As shown in FIG. 9A, first plurality of teeth (364A) of first arm (367A) of firing beam (362) and first plurality of teeth (345) of elongate member (344) engage teeth (365) of first gear (366) on opposites sides of first gear (366). Also as shown in FIG. 9A, second plurality of teeth (364B) of second arm (367B) of firing beam (362) and teeth (347) of elongate member (344) engage teeth (369) of second gear (368) on opposites sides of second gear (368). Therefore, it should be understood that longitudinal movement of elongate member (344) in a first direction will cause longitudinal movement of firing beam (362) in a second direction.

Trigger (340) may slide longitudinally relative to body (320) within an elongate slot (324). Initially, trigger (340) remains in a distal position as shown in FIG. 9A. When trigger (340) is in this distal position, firing beam (362) remains in a proximal position as shown in FIG. 9A. Once tissue has been captured between first jaw (334) and second jaw (332), the user may begin to pull trigger (340) in a proximal direction within elongate slot (324). As the user begins to pull trigger (340) proximally, the force required to do so will cause a button (342) to be depressed thereby causing RF energy to be delivered into the tissue captured between first jaw (334) and second jaw (332) via electrodes in jaws (332, 334). Therefore it should be understood that RF energy will be delivered into the tissue captured between first jaw (334) and second jaw (332) prior to the tissue being severed by blade insert (394). As the user continues to pull trigger (340) proximally, button (342) remains depressed and RF energy is continually delivered to the tissue captured between first jaw (334) and second jaw (332).

As trigger (340) is moved into a proximal position as shown in FIG. 9B, the longitudinal movement of trigger (340) causes elongate member (344) to be moved proximally as well. The proximal longitudinal movement of elongate member (344) causes first gear (366) to be rotated in a CCW direction about third pin (325). The proximal longitudinal movement of elongate member (344) also causes second gear (368) to be rotated in a CW direction about fourth pin (326). The combination of CCW rotation of first gear (366) and CW rotation of second gear (368) causes distal longitudinal movement of firing beam (362). Such distal longitudinal movement of firing beam (362) will drive blade insert (394) to sever the tissue captured between first jaw (334) and second jaw (332). After the tissue has been severed, the user may draw firing beam (362) proximally by moving trigger (340) distally.

While FIG. 9B shows a particular distance between sharp distal edge (396) and the distal tips of jaws (332, 334) upon completion of the distal advancement stroke of firing beam (362), it should be understood that forceps (300) may be configured such that this distance may be reduced relative to what is shown in FIG. 9B. For instance, forceps (300) may be configured such that sharp distal edge (396) reaches the distal tips of jaws (332, 334) (or a location just barely proximal to the distal tips of jaws (332, 334)) upon completion of the distal advancement stroke of firing beam (362). This may reduce any likelihood of tissue between jaws (332, 334) being left unsevered upon completion of the distal advancement stroke of firing beam (362).

The steps of capturing tissue between first jaw (334) and second jaw (332), severing tissue with blade insert (394), and drawing firing beam (362) from the tissue, may be repeated as many times as desired. It should be understood, that although in the present example the user manually draws firing beam (362) proximally from the tissue by moving trigger (340) distally, such proximal movement of firing beam (362) may be caused by a biasing member (not shown) which drives trigger (340) in a distal direction once the user has released trigger (340). For instance, a spring, or a plurality of springs, may be positioned to bias trigger (340) distally.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010; now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body, wherein the body comprises:
      (i) a distal end,
      (ii) a proximal end,
      (iii) a first pin, and
      (iv) a second pin,
      wherein the body defines an elongate opening, wherein the proximal end of the body defines a first scissor grip;
   (b) an end effector, wherein the end effector comprises a first jaw and a second jaw, and wherein the first jaw is selectively pivotable toward and away from the second jaw about a first axis, wherein the second jaw is fixed relative to the body;
   (c) a lever pivotably coupled to the body about the first axis, wherein the lever comprises a distal end and a proximal end, wherein the first jaw is coupled to the distal end of the lever, wherein the lever is configured to drive the first jaw toward and away from the second jaw, wherein the proximal end of the lever defines a second scissor grip; and
   (d) a tissue severing assembly, wherein the tissue severing assembly comprises:
      (i) a gear, wherein the gear is rotatable about a first second axis,
      (ii) a longitudinally sliding trigger, wherein the longitudinally sliding trigger is slidably disposed within the elongate opening,
      (iii) an elongate member extending distally from the longitudinally sliding trigger, wherein the elongate member is fixed to the longitudinally sliding trigger, wherein the elongate member defines a first longitudinal slot, wherein the second pin is slidably disposed within the first longitudinal slot, wherein the elongate member is engaged with the gear, and
      (iv) a firing beam engaged with the gear, wherein the firing beam defines a second longitudinal slot, wherein the first pin is slidably disposed within the second longitudinal slot, wherein the longitudinally sliding trigger is operable to drive the firing beam.

2. The apparatus of claim 1, wherein the gear comprises a first side and a second side, wherein the first side is located opposite the second side, wherein a portion of the elongate member is positioned on the first side of the gear, wherein a portion of the firing beam is positioned on the second side of the gear.

3. The apparatus of claim 1, wherein the firing beam comprises a distal end, and wherein the firing beam further comprises a blade positioned at the distal end of the firing beam, wherein the blade is configured to sever tissue captured between the first and the second jaws.

4. The apparatus of claim 1, wherein the end effector comprises at least one electrode operable to apply radiofrequency (RF) energy to tissue.

5. The apparatus of claim 4, wherein the longitudinally sliding trigger further comprises a button, and wherein the button is operable to selectively activate the at least one electrode to thereby apply the radiofrequency (RF) energy.

6. The apparatus of claim 5, wherein the longitudinally sliding trigger is configured to be immovable unless the button is depressed.

7. The apparatus of claim 5, wherein the button is configured to be unable to be depressed unless the end effector is in a closed position.

8. The apparatus of claim 5, wherein the button and the longitudinally sliding trigger are configured to move in a same direction.

9. The apparatus of claim 1, wherein the longitudinally sliding trigger is configured to be immovable unless the end effector is in a closed position.

10. The apparatus of claim 1, wherein the longitudinally sliding trigger is positioned distal to the first and the second scissor grips.

11. The apparatus of claim 1, wherein the elongate opening encompasses the longitudinally sliding trigger.

12. The apparatus of claim 11, wherein the longitudinally sliding trigger is annular, wherein the elongate opening comprises a proximal end and a distal end, wherein the proximal end and the distal end each define a shape complementing the longitudinally sliding trigger.

13. An apparatus comprising:
   (a) a body, wherein the body comprises a distal end and a proximal end, wherein the body defines an elongate opening, wherein the proximal end of the body defines a first scissor grip;
   (b) an end effector, wherein the end effector comprises a first jaw and a second jaw, and wherein the first jaw is selectively pivotable toward and away from the second jaw, wherein the end effector comprises at least one electrode operable to apply radiofrequency (RF) energy to tissue;
   (c) a lever pivotably coupled to the body, wherein the lever comprises a distal end and a proximal end, wherein the first jaw is coupled to the distal end of the lever, wherein the lever is configured to drive the first jaw toward and away from the second jaw, wherein the proximal end of the lever defines a second scissor grip; and (d) a tissue severing assembly, wherein the tissue severing assembly comprises:
  (i) a pinion gear,
  (ii) a longitudinally sliding trigger, wherein the longitudinally sliding trigger is slidably disposed within the elongate opening,
  (iii) a button configured to activate the end effector to apply radiofrequency (RF) energy to tissue when moved from a first position to a second position, wherein the first position and the second position are located along a longitudinal axis defined by the body, wherein the button is disposed within the longitudinally sliding trigger, wherein the button moves from the first position to the second position along the same direction as the longitudinally sliding trigger, wherein the radiofrequency (RF) energy is activated only when the button and the longitudinally sliding trigger simultaneously slide from the first position to the second position,
  (iv) an elongate member further comprising a proximal end, a distal end, and a first rack configured to mesh with the pinion gear, wherein the distal end of the elongate member is fixed to the longitudinally sliding trigger, and
  (v) a longitudinally sliding firing beam comprising a second rack, wherein the second rack is configured to mesh with the pinion gear,
  wherein the longitudinally sliding trigger is longitudinally movable in a proximal direction to cause distal longitudinal movement of the longitudinally sliding firing beam.

14. The apparatus of claim 13, wherein the longitudinally sliding trigger is longitudinally movable in a distal direction to cause proximal longitudinal movement of the firing beam.

15. The apparatus of claim 13, wherein the first jaw and the lever both pivot about a same axis.

16. An apparatus comprising:
(a) a body, wherein the body comprises a distal end and a proximal end, wherein the body defines an elongate opening, wherein the proximal end of the body defines a first scissor grip;
(b) an end effector, wherein the end effector comprises a first jaw and a second jaw, and wherein the first jaw is selectively pivotable toward and away from the second jaw, wherein the end effector further comprises at least one electrode operable to provide radiofrequency (RF) energy to tissue;
(c) a lever pivotably coupled to the body, wherein the lever comprises a distal end and a proximal end, wherein the first jaw is coupled to the distal end of the lever, wherein the lever is configured to drive the first jaw toward and away from the second jaw, wherein the proximal end of the lever defines a second scissor grip;
(d) a tissue severing assembly, wherein the tissue severing assembly comprises:
  (i) a longitudinally sliding trigger, wherein the longitudinally sliding trigger is slidably disposed within the elongate opening of the body, wherein the longitudinally sliding trigger defines an opening, wherein the longitudinally sliding trigger is movable along a first plane of motion,
  (ii) a button, wherein the button is disposed within the opening of the longitudinally sliding trigger, wherein the button is movable relative to the longitudinally sliding trigger along the first plane in order to selectively activate the at least one electrode with the radiofrequency (RF) energy, and
  (iii) a longitudinally sliding firing beam, wherein the longitudinally sliding trigger is operable to advance the longitudinally sliding firing beam distally in response to a proximal movement of the longitudinally sliding trigger;
(e) a lockout feature configured to prevent the proximal movement of the longitudinally sliding trigger until the button is depressed.

* * * * *